United States Patent [19]

Cruickshank et al.

[11] Patent Number: 4,514,419
[45] Date of Patent: Apr. 30, 1985

[54] NEMATICIDAL USE OF HYDRAZINECARBOXAMIDES AND CARBOTHIOAMIDES

[75] Inventors: Philip A. Cruickshank, Princeton; Carmine P. DiSanzo, Lawrenceville, both of N.J.; Kiyosi Kondo, Kanagawa; Hiromichi Kono, Yamaguchi, both of Japan

[73] Assignees: FMC Corporation; Kanagawa Chemical Laboratory, Ltd., both of Tokyo, Japan

[21] Appl. No.: 495,859

[22] Filed: May 18, 1983

Related U.S. Application Data

[63] Continuation-in-part of Ser. No. 375,424, May 6, 1982, abandoned.

[51] Int. Cl.³ .................................................. A01N 33/26
[52] U.S. Cl. .................................. 514/521; 260/465 D; 260/465 E; 564/18; 564/34; 514/581; 514/590
[58] Field of Search ................................ 424/304, 323; 260/465 D, 465 E; 564/18, 34

[56] References Cited

U.S. PATENT DOCUMENTS 3,067,250 12/1962 Oja ........................................ 564/18
3,318,680 5/1967 Levitt ................................. 564/18 X
4,282,031 8/1981 Rutter et al. ............................ 71/99

OTHER PUBLICATIONS

*Chemical Abstracts*, vol. 71, 3166k, (1969).
*Chemical Abstracts*, vol. 75, 109975w, (1971).
*Chemical Abstracts*, vol. 88, 70491b, (1978).

Primary Examiner—Dolph H. Torrence
Attorney, Agent, or Firm—R. L. Hansen; H. R. Ertelt

[57] ABSTRACT

Hydrazinecarboxamides and carbothioamides of the formula

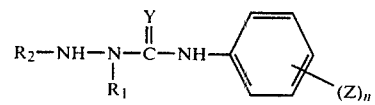

wherein $R_1$ is selected from alkyl, cyanoalkyl, hydroxyalkyl, and benzyl, $R_2$ is hydrogen or alkyl, Y is oxygen or sulfur, n is 0–5, and Z is substituted for hydrogen and independently selected from halogen, alkyl, alkoxy, phenoxy, trifluoromethyl, and nitro are useful as nematicides when applied to or incorporated into nematode-infested soil.

18 Claims, No Drawings

NEMATICIDAL USE OF HYDRAZINECARBOXAMIDES AND CARBOTHIOAMIDES

This is a continuation in part of application Ser. No. 375,424 filed May 6, 1982, now abandoned.

This invention relates to chemical compositions as well as a method of using the compositions to control nematodes, especially on agricultural crops. More specifically, the nematicidal compositions contain hydrazinecarboxamide or carbothioamide derivatives as the active nematicidal agent.

Hydrazinecarboxamide and hydrazinecarbothioamide have been variously named in the chemical literature. For example, they have been called semicarbazine and thiosemicarbazine, or semicarbazide and thiosemicarbazide, respectively. Such compounds are of the formula

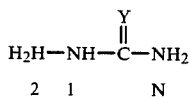

wherein Y is oxygen or sulfur, respectively, and the sites of potential substitution are designated.

Compounds of this general type have been disclosed in the art. Some compounds of this type are known to exhibit insecticidal activity; for example, 2-phenylthiosemicarbazide [*Chemical Abstracts*, 39, 764⁴ (1945)], 2,N-diphenylthiosemicarbazide [U.S. Pat. No. 2,403,495], and N-(substituted phenyl)-2-cyanoethylthiosemicarbazide [Derwent Japanese Patents Gazette, Section Ch: Chemical, Week B46, Acc. No. 83180-B, Jan. 2, 1980]. Compounds of this general type have also been disclosed to exhibit herbicidal activity [*Chem. Abstr.*, 88, 70491b and 104867w (1978)]. Finally, certain compounds of this type are known as nematicides; for example, N-methylthiosemicarbazide [*Chem. Abstr.*, 55, 19123i (1961)] and 2-(p-aminophenyl)semicarbazide [*Chem. Abstr.*, 54, 16729h (1960)].

According to the present invention, hydrazinecarboxamides and carbothioamides of the following structural formula, some of which are novel compounds, control nematodes when applied to soil or other locus per se or as suitably formulated nematicidal compositions:

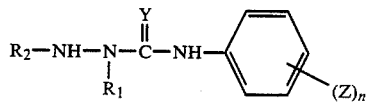

With reference to the aforesaid structural formula, the compounds useful as nematicides include those wherein $R_1$ is selected from alkyl, cyanoalkyl, hydroxyalkyl, and benzyl,
$R_2$ is hydrogen or alkyl,
Y is sulfur or oxygen,
n is 0–5, and
Z is substituted for hydrogen and independently selected from halogen, alkyl, alkoxy, phenoxy, trifluoromethyl, and nitro.

Within the aforesaid description, it is preferred that alkyl and alkoxy be limited to chains, either straight or branched, containing 1–6, preferably 1–4 carbon atoms, especially 1–2 carbon atoms. Although the term "halogen" is intended to encompass fluorine, chlorine, bromine, and iodine, the halogen is preferably selected from fluorine, chlorine, and bromine, especially chlorine and bromine. It is further preferred that Y be sulfur, the compounds of greatest interest being hydrazinecarbothioamides.

Furthermore, it is preferred that $R_1$ be selected from alkyl, cyanoalkyl, and hydroxyalkyl; among these, methyl, 2-cyanoethyl, and 2-hydroxyethyl are preferred, but the compounds of greatest interest are those wherein $R_1$ is methyl.

Among the substituents $(Z)_n$ it is preferred that Z be independently selected from fluorine, chlorine, bromine, methyl, ethyl (when $R_2$ is hydrogen), trifluoromethyl, nitro, and phenoxy. Compounds of the above formula in which the $(Z)_n$ are independently selected from trifluoromethyl, nitro, and phenoxy are novel compounds within the scope of this invention. It is most preferred that Z be independently selected from fluorine, chlorine, bromine, and methyl, especially when n is 1 or 2.

Compounds of particular interest for use as nematicides include N-(2,3-dichlorophenyl)-1-methylhydrazinecarbothioamide, N-(2,4-dichlorophenyl)-1-methylhydrazinecarbothioamide, N-(2,5-dichlorophenyl)-1-methylhydrazinecarbothioamide, N-(2,6-dichlorophenyl)-1-methylhydrazinecarbothioamide, N-(4-bromophenyl)-1-methylhydrazinecarbothioamide, N-(2,5-dibromophenyl)-1-methylhydrazinecarbothioamide, N-(2-chloro-6-methylphenyl)-1-methylhydrazinecarbothioamide, N-(3-chloro-2-methylphenyl)-1-methylhydrazinecarbothioamide, N-(4-chloro-2-methylphenyl)-1-methylhydrazinecarbothioamide, N-(5-chloro-2-methylphenyl)-1-methylhydrazinecarbothioamide, N-(4-bromo-2-methylphenyl)-1-methylhydrazinecarbothioamide, N-(4-chlorophenyl)-1,2-dimethylhydrazinecarbothioamide, N-(4-chlorophenyl)-1-methylhydrazinecarbothioamide, N-(2,4-dichlorophenyl)-1,2-dimethylhydrazinecarbothioamide, N-(2,5-dichlorophenyl)-1,2-dimethylhydrazinecarbothioamide, N-(3,4-dichlorophenyl)-1,2-dimethylhydrazinecarbothioamide, N-(4-bromophenyl)-1,2-dimethylhydrazinecarbothioamide, N-(2,6-difluorophenyl)-1,2-dimethylhydrazinecarbothioamide, N-(4-bromo-2-chlorophenyl)-1,2-dimethylhydrazinecarbothioamide, N-(3-chloro-2-methylphenyl)-1,2-dimethylhydrazinecarbothioamide, N-(4-chloro-2-methylphenyl)-1,2-dimethylhydrazinecarbothioamide, N-(5-chloro-2-methylphenyl)-1,2-dimethylhydrazinecarbothioamide, N-(4-bromo-2-methylphenyl)-1,2-dimethylhydrazinecarbothioamide, N-(3,4-dichlorophenyl)-1-methylhydrazinecarbothioamide, N-(4-chlorophenyl)-1-(2-hydroxyethyl)hydrazinecarbothioamide, N-(4-chlorophenyl)-1-(2-cyanoethyl)hydrazinecarbothioamide, N-(4-bromophenyl)-1-(2-cyanoethyl)hydrazinecarbothioamide, N-(2-chlorophenyl)-1,2-dimethylhydrazinecarbothioamide, N-(4-chlorophenyl)-1,2-dimethylhydrazinecarboxamide, N-(4-bromophenyl)-1,2-dimethylhydrazinecarboxamide, N-(2-chlorophenyl)-1,2-dimethylhydrazinecarboxamide, N-(3-chlorophenyl)-1,2-dimethylhydrazinecarboxamide, N-(4-methylphenyl)-1,2-dimethylhydrazinecarboxamide, N-(4-bromo-2-methylphenyl)-1-(2-hydroxyethyl)hydrazinecarbothioamide, N-(2,4-dichlorophenyl)-1-(2-hydroxyethyl)hydrazinecarbothioamide, N-(4-chloro-2-methylphenyl)-1-(2-cyanoethyl)hydrazinecarbothioamide, N-(4-bromo-2-methylphenyl)-1-(2-cyanoethyl)-hydrazinecarbothioamide, and 1,2-dimethyl-N-(4-nitrophenyl)hydrazinecarbothioamide.

Among the just named compounds, N-(4-chlorophenyl)-1,2-dimethylhydrazinecarbothioamide, N-(4-chlorophenyl)-1-methylhydrazinecarbothioamide, N-(5-chloro-2-methylphenyl)-1-methylhydrazinecarbothioamide, N-(4-bromo-2-methylphenyl)-1-methylhydrazinecarbothioamide, N-(4-chlorophenyl)-1-(2-cyanoethyl)hydrazinecarbothioamide, N-(4-bromophenyl)-1-(2-cyanoethyl)hydrazinecarbothioamide, N-(4-chlorophenyl)-1,2-dimethylhydrazinecarboxamide, N-(4-bromophenyl)-1,2-dimethylhydrazinecarboxamide, N-(3-chlorophenyl)-1,2-dimethylhydrazinecarboxamide, N-(4-bromo-2-methylphenyl)-1-(2-hydroxyethyl)hydrazinecarbothioamide, and N-(2,4-dichlorophenyl)-1-(2-hydroxyethyl)hydrazinecarbothioamide, display especially high nematicidal activity.

The nematicidal compounds are readily prepared by adding hydrazine derivatives carrying appropriate $R_1$ and $R_2$ substituents to phenylisocyanate or phenylisothiocyanate derivatives in which the phenyl rings carry the desired substituents $(Z)_n$. The hydrazine, isocyanate, and isothiocyanate starting materials are generally available in commerce, or can be made by preparative methods known in the art. These syntheses are illustrated in Examples 1 and 2 below. Other nematicidal hydrazinecarboxamides and carbothioamides are prepared by similar methods, the identities of the compounds being established by reference to elemental analysis and physical properties. Representative nematicidal hydrazinecarboxamides and carbothioamides are listed in Table 1.

EXAMPLE 1

N-(4-chlorophenyl)-1-methylhydrazinecarbothioamide

A mixture of 4-chlorophenylisothiocyanate (17.0 g, 0.10 mole) and methylhydrazine (5.0 g, 0.11 mole) in 80 ml of ethanol was stirred at room temperature for two hours. The reaction mixture was filtered to collect colorless crystalline N-(4-chlorophenyl)-1-methylhydrazinecarbothioamide (18.4 g, mp 152°–154° C.).

Analysis: Calc'd for $C_8H_{10}ClN_3S$: C, 44.55; H, 4.68; N, 19.48; S, 14.86; Cl, 16.44. Found: C, 44.64; H, 4.64; N, 19.32; S, 15.01; Cl, 16.47.

EXAMPLE 2

N-(4-chlorophenyl)-1,2-dimethylhydrazinecarbothioamide

To a stirred solution of sodium hydroxide (6.1 g, 0.15 mole) in 40 ml of water and 250 ml of ethanol was added N,N'-dimethylhydrazine dihydrochloride (10 g, 0.076 mole). The reaction mixture was warmed to 50° C., and 4-chlorophenylisothiocyanate (12.8 g, 0.076 mole) was added in small portions. Upon complete addition, the reaction mixture was heated under reflux for two hours and then allowed to cool. The cooled reaction mixture was filtered and the filtrate concentrated under reduced pressure to remove most of the solvent. The concentrate was taken up in 200 ml of toluene. The toluene was removed under reduced pressure. This procedure was repeated with two additional 200 ml portions of toluene to remove the remaining ethanol and water traces by azeotropic distillation. The brown residual oil was recrystallized twice from ethanol to give N-(4-chlorophenyl)-1,2-dimethylhydrazinecarbothioamide (6.8 g, mp 103°–104° C.). The nmr spectrum of the product was consistent with the assigned structure.

In the normal use of the aforesaid nematicidal hydrazinecarboxamides and carbothioamides, the nematicidal compounds usually will not be employed free from admixture or dilution, but ordinarily will be used in a suitable formulated nematicidal composition compatible with the method of application and comprising a nematicidally effective amount of at least one of said nematicidal compounds. Said nematicidal compounds, like most pesticidal agents, may be blended with the agriculturally acceptable surface-active agents and carriers normally employed for facilitating the dispersion of active ingredients, recognizing the accepted fact that the formulation and mode of application of a nematicidal compound may affect the activity of the material. The present nematicidal compounds may be applied, for example, as sprays, dusts, or granules to the area where pest control is desired, the type of application varying of course with the pest and the environment. Thus, the nematicidal compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said nematicidal compounds. The granule particles are relatively large, a diameter of about 400–2500 microns typically. The particles are either impregnated with the nematicidal compound from solution or coated with the compound, adhesive sometimes being employed. Granules generally contain 0.05–10%, preferably 0.5–5%, active ingredient as the nematicidally effective amount. A typical granular formulation employed for evaluation purposes contains 95% attapulgite clay (24/48 mesh) and 5% N-(4-chlorophenyl)-1,2-dimethylcarbothioamide by weight.

Dusts are admixtures of said nematicidal compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the nematicide. These finely divided solids have an average particle size of less than about 50 microns. A typical dust formulation useful for controlling nematodes contains by weight 5 parts N-(4-chlorophenyl)-1,2-dimethylcarbothioamide, 91.2 parts attapulgite clay, 1.9 parts sodium lignosulfonate, and 1.9 parts sodium alkylnaphthalene sulfonate.

The nematicidal compounds of the present invention may be made into liquid concentrates by dissolution or emulsification in suitable liquids and into solid concentrates by admixture with talc, clays, and other known solid carriers used in the pesticide art. The concentrates are compositions containing, as a nematicidally effective amount, about 5–50% the nematicidal compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the nematicidal compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the nematicidal composition.

Other useful formulations include simple solutions of the active ingredient in a solvent in which it is completely soluble at the desired concentration, such as acetone or other organic solvents.

A nematicidally effective amount of said nematicidal compound in a nematicidal composition diluted for application is normally in the range of about 0.001% to about 8% by weight. Many variations of spraying and dusting compositions known in the art may be used by substituting said nematicidal compounds of this invention into compositions known or apparent to the art.

The nematicidal compositions of this invention may be formulated with other active ingredients, including insecticides, other nematicides, acaricides, fungicides, plant growth regulators, fertilizers, etc. In using the compositions to control nematodes, it is only necessary that a nematicidally effective amount of at least one of said nematicidal compounds be applied to the locus where control is desired, generally a soil locus where agricultural crops are grown. When applied to soil, it is advantageous to mix or incorporate the nematicidal compound into the soil. Liquid nematicidal compositions may be injected into the soil as fumigants or sprayed on the surface. Solid compositions may be applied by broadcasting or in bands. For most applications, a nematicidally effective amount will be about 75 to 4000 g per hectare, preferably 150 g to 3000 g per hectare.

The nematicidal compounds were evaluated for nematicidal activity against the root-knot nematode (*Meloidogyne incognita*), the stunt nematode (*Tylenchorhynchus claytoni*), and the lesion nematode (*Pratylenchus penetrans*) using standard 5 weight percent dust formulations made up as follows and ground to fine powders:

| | |
|---|---|
| Nematicidal compound (100% active basis) | 5 parts |
| Base | 95 parts |
| 96% attapulgite clay | |
| 2% highly purified sodium lignosulfonate (100%) | |
| 2% powdered sodium alkylnaphthalenesulfonate (75%) | |

The formulations were tested for activity against root-knot nematode as follows.

Nematode Culture

Tomato seedlings with two large true leaves were transplanted into six inch clay pots containing steam-sterilized sandy soil. One week after transplanting, galled roots of nematode-infected tomato plants, with fully developed nematode egg masses, were placed in three holes in the soil around the seedling roots. The holes were then closed with soil and the plants were allowed to grow until fully developed nematode egg masses were formed (6 to 7 weeks).

Inoculum Preparation

Infected tomato roots containing egg masses were cleaned under running tap water, cut into short pieces, and comminuted with water in an electric blender for 30 seconds. The shredded roots were poured onto washed sand in a wooden flat. The flat was covered with plastic sheeting and kept at greenhouse temperatures for 3 to 7 days, allowing about 50% of the nematode eggs to hatch.

Preparation of Root-Knot Nematode Infested Soil

Samples of the inoculum prepared as described above were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue", *Proc. Helm. Soc., Washington*, 22, 87–89 (1955).]

Fine wire cloth screen (No. 500, U.S.A. Standard Sieve Series) was used to collect the nematodes and eggs, and their number was estimated under a stereomicroscope. Enough inoculum was mixed with additional steam-sterilized sandy soil so that there were 600 to 800 root-knot nematode larvae and eggs per pot of soil (three inch diameter each, containing approximately 300 g soil). Depending on the total amount of nematode infested soil needed, mixing was accomplished by use of a cement mixer for 5 minutes or a V-shaped rotary mixer for 60 seconds.

Soil so infested was used for soil-incorporated nematicidal studies within 2 days of preparation. The infested soil was treated with dust formulations to be tested for nematicidal activity by incorporating the dust in the soil at 25 ppm or less (weight active compound in mg/soil volume in liters). Young tomato plants were planted in this treated, infested soil in three-inch pots. Check plants were planted in the same manner, except untreated, infested soil was used. The formulation base, without active ingredient, was added to infested soil separately and tomato plants grown therein to detect the effects, if any, of chemicals in the formulation base.

At the end of two weeks the roots of all plants were examined and evaluated for galling in comparison to untreated check plants. The results of the tests were expressed in terms of a "Galling Index", a galling index of 4 signifying no control, 3 signifying 25% less swelling on the treated roots than the untreated roots, 2 signifying 50% less swelling, 1 signifying 75% less swelling, and 0 signifying complete control. Between 1 and 0, a galling index of 0.8, 0.5, and 0.4–0.1 signifies 80%, 90%, and 95–99% control, respectively. The results of tests at 25 ppm against the root-knot nematode using a number of nematicidal hydrazinecarboxamides and carbothioamides appear in Table 1.

Evaluation of compositions of the invention against stunt nematode was carried out by incorporating 5% dust formulations in soil at various concentrations and then planting a corn seedling therein. Two days thereafter the soil was inoculated with stunt nematode in mixed stages of growth, from larvae to adults. The soil was evaluated for nematode population approximately five weeks after treatment. Untreated check plants showed no nematode control. Results are recorded in Table 2 as "Percent Control" relative to nematode control in the untreated check pot. The results appear in Table 2.

Compositions were also evaluated against lesion nematode, following a procedure similar to that for stunt nematode, but in which pea seedlings were planted instead of corn seedlings, and nematodes were extracted from the root systems, instead of from the soil. Untreated plants showed no nematode control. Results with formulations of the invention are recorded in Table 3.

TABLE 1

| Compound Number | Nematicidal Compounds and Properties | | |
|---|---|---|---|
| | Name | mp (°C.) | Galling Index |
| 1 | N—(4-Chlorophenyl)-1-methyl-hydrazinecarbothioamide | 152–154 | 0 |
| 2 | N—(4-Chlorophenyl)-1,2-dimethyl-hydrazinecarbothioamide | 105–105.5 | 0 |
| 3 | 1-Methyl-N—phenylhydrazine-carbothioamide | 148–150 | 0 |
| 4 | N—(3-Chlorophenyl)-1-methyl-hydrazinecarbothioamide | | 0 |
| 5 | N—(2,3-Dichlorophenyl)-1-methyl-hydrazinecarbothioamide | 127–128 | 0 |
| 6 | N—(2,4-Dichlorophenyl)-1-methyl-hydrazinecarbothioamide | 170–172 | 0 |
| 7 | N—(2,5-Dichlorophenyl)-1-methyl-hydrazinecarbothioamide | 151.5 ∝ 152.5 | 0 |
| 8 | N—(2,6-Dichlorophenyl)-1-methyl-hydrazinecarbothioamide | 162–168 | 0 |
| 9 | N—(3,4-Dichlorophenyl)-1-methyl-hydrazinecarbothioamide | 149–150 | 2.5 |
| 10 | 1-Methyl-N—(2,4,6-trichlorophenyl-hydrazinecarbothioamide | 183–185 | 0.25 |
| 11 | N—(2-bromophenyl)-1-methyl-hydrazinecarbothioamide | 172–174 | 0 |
| 12 | N—(3-bromophenyl)-1-methyl-hydrazinecarbothioamide | 191–192 | 0.25 |
| 13 | N—(4-Bromophenyl)-1-methyl-hydrazinecarbothioamide | 149–150 | 0 |
| 14 | N—(2,5-Dibromophenyl)-1-methyl-hydrazinecarbothioamide | 175–178 | 0 |
| 15 | 1-Methyl-N—(2,4,6-tribromophenyl)-hydrazinecarbothioamide | 191–192 | 1.5 |
| 16 | N—(3-Fluorophenyl)-1-methyl-hydrazinecarbothioamide | 122–124 | 0 |
| 17 | N—(2,6-Difluorophenyl)-1-methyl-hydrazinecarbothioamide | 191–193 | 0 |
| 18 | 1-Methyl-N—(2,3,4,6-tetrafluoro-phenyl)hydrazinecarbothioamide | 145–147 | 0 |
| 19 | N—(4-Bromo-2-chlorophenyl)-1-methylhydrazinecarbothioamide | 173–175 | 0 |
| 20 | N—(2-Chloro-6-methylphenyl)-1-methylhydrazinecarbothioamide | 152–155 | 0 |
| 21 | N—(3-Chloro-2-methylphenyl)-1-methylhydrazinecarbothioamide | 163–164 | 0 |
| 22 | N—(3-Chloro-4-methylphenyl)-1-methylhydrazinecarbothioamide | 158–160 | 0 |
| 23 | N—(4-Chloro-2-methylphenyl)-1-methylhydrazinecarbothioamide | 151–153 | 0 |
| 24 | N—(5-Chloro-2-methylphenyl)-1-methylhydrazinecarbothioamide | 152–153 | 0 |
| 25 | N—(2-Bromo-4-methylphenyl)-1-methylhydrazinecarbothioamide | 165–168 | 0 |
| 26 | N—(4-Bromo-2-methylphenyl)-1-methylhydrazinecarbothioamide | 157–158 | 0 |
| 27 | N—(4-Bromo-2,6-dimethylphenyl)-1-methylhydrazinecarbothioamide | 177–179 | 0.9 |
| 28 | 1-Methyl-N—(2-methylphenyl)-hydrazinecarbothioamide | 176–177 | 1 |
| 29 | 1-Methyl-N—(4-methylphenyl)-hydrazinecarbothioamide | 164–166 | 0.4 |
| 30 | N—(2,6-Dimethylphenyl)-1-methyl-hydrazinecarbothioamide | 165–168 | 0.4 |
| 31 | N—(3,4-Dimethylphenyl)-1-methyl-hydrazinecarbothioamide | 165–167 | 0 |
| 32 | 1-Methyl-N—(2,4,6-trimethylphenyl)-hydrazinecarbothioamide | 182–184 | 1.5 |
| 33 | N—(3-Ethylphenyl)-1-methyl-hydrazinecarbothioamide | 136–137 | 0.4 |
| 34 | N—(4-Ethylphenyl)-1-methyl-hydrazinecarbothioamide | 138–140 | 0 |
| 35 | 1-Methyl-N—(4-trifluoromethyl-phenyl)hydrazinecarbothioamide | 158–159 | 0 |
| 36 | 1-Methyl-N—(4-nitrophenyl)-hydrazinecarbothioamide | 178–179 | 0 |
| 37 | 1-Methyl-N—(4-phenoxyphenyl)-hydrazinecarbothioamide | 143–144 | 1 |
| 38 | 1-(2-Hydroxyethyl)-N—phenyl-hydrazinecarbothioamide | Liquid | 0.5 |
| 39 | N—(4-Chlorophenyl)-1-(2-hydroxy-ethyl)hydrazinecarbothioamide | 123–125 | 0 |
| 40 | N—(2,5-Dichlorophenyl)-1-(2-hydroxyethyl)hydrazine-carbothioamide | | 0.1 |
| 41 | N—(4-Bromophenyl)-1-(2-hydroxy-ethyl)hydrazine-carbothioamide | 141–142 | 0 |
| 42 | N—(3-Chloro-2-methylphenyl)-1-(2-hydroxyethyl)hydrazine-carbothioamide | | 0.25 |
| 43 | N—(4-Chloro-2-methylphenyl)-1-(2-hydroxyethyl)hydrazine-carbothioamide | | 0 |
| 44 | 1-(2-Hydroxyethyl)-N—(4-methyl-phenyl)hydrazinecarbothioamide | 124–127 | 1.5 |
| 45 | 1-(2-hydroxyethyl)-N—(3,4-dimethyl-phenyl)hydrazinecarbothioamide | 80–85 | 0 |
| 46 | N—(4-Ethylphenyl)-1-(2-hydroxy-ethyl)hydrazinecarbothioamide | 87–93 | 0.4 |
| 47 | N—[4-(Trifluoromethyl)phenyl]-1-(2-hydroxyethyl)hydrazine-carbothioamide | 139–141 | 0 |
| 48 | 1-(2-Hydroxyethyl)-N—(4-nitro-phenyl)hydrazinecarbothioamide | 122–132 | 1.5 |
| 49 | 1-(2-Cyanoethyl)-N—phenylhydra-zinecarbothioamide | Liquid | 0.4 |
| 50 | N—(4-Chlorophenyl)-1-(2-cyano-ethyl)hydrazinecarbothioamide | 105–107 | 0 |
| 51 | N—(4-Bromophenyl)-1-(2-cyano-ethyl)hydrazinecarbothioamide | Liquid | 0.5 |
| 52 | 1-(2-Cyanoethyl)-N—(4-methyl-phenyl)hydrazinecarbothioamide | Liquid | 3 |
| 53 | 1,2-Dimethyl-N—phenylhydrazine-carbothioamide | 110–111 | 0 |
| 54 | N—(2-Chlorophenyl)-1,2-dimethyl-hydrazinecarbothioamide | 152–154 | 0 |
| 55 | N—(2,3-Dichlorophenyl)-1,2-dimethylhydrazinecarbothioamide | 128–132 | 1 |
| 56 | N—(2,4-Dichlorophenyl)-1,2-dimethylhydrazinecarbothioamide | 133–134 | 0 |
| 57 | N—(2,5-Dichlorophenyl)-1,2-dimethylhydrazinecarbothioamide | 110–115 | 1.4 |
| 58 | N—(2,6-Dichlorophenyl)-1,2-dimethylhydrazinecarbothioamide | 188–190 | 2.5 |

TABLE 1-continued
Nematicidal Compounds and Properties

| Compound Number | Name | mp (°C.) | Galling Index |
|---|---|---|---|
| 59 | N—(3,4-Dichlorophenyl)-1,2-dimethylhydrazinecarbothioamide | 108–109 | 0.65 |
| 60 | 1,2-Dimethyl-N—(2,4,6-trichlorophenyl)hydrazinecarbothioamide | 176–182 | 0.75 |
| 61 | N—(2-Bromophenyl)-1,2-dimethylhydrazinecarbothioamide | 159–161 | 0 |
| 62 | N—(3-Bromophenyl)-1,2-dimethylhydrazinecarbothioamide | 125–129 | 0.75 |
| 63 | N—(4-Bromophenyl)-1,2-dimethylhydrazinecarbothioamide | 103–105 | 0 |
| 64 | N—(3-Fluorophenyl)-1,2-dimethylhydrazinecarbothioamide | 72–75 | 0 |
| 65 | N—(2,6-Difluorophenyl)-1,2-dimethylhydrazinecarbothioamide | 172–180 | 0.65 |
| 66 | 1,2-Dimethyl-N—(2,3,4,6-tetrafluorophenyl)hydrazinecarbothioamide | 138–139 | 1 |
| 67 | 1,2-Dimethyl-N—(2-iodophenyl)hydrazinecarbothioamide | 161–166 | 0.35 |
| 68 | N—(4-Bromo-2-chlorophenyl)-1,2-dimethylhydrazinecarbothioamide | 110–1136 | 0 |
| 69 | N—(2-Chloro-4-methylphenyl)-1,2-dimethylhydrazinecarbothioamide | 134–139 | 2.5 |
| 70 | N—(2-Chloro-6-methylphenyl)-1,2-dimethylhydrazinecarbothioamide | 151–155 | |
| 71 | N—(3-Chloro-2-methylphenyl)-1,2-dimethylhydrazinecarbothioamide | 135–140 | 1.5 |
| 72 | N—(3-Chloro-4-methylphenyl)-1,2-dimethylhydrazinecarbothioamide | 101–105 | 1 |
| 73 | N—(4-Chloro-2-methylphenyl)-1,2-dimethylhydrazinecarbothioamide | 147–148 | 0.4 |
| 74 | N—(5-Chloro-2-methylphenyl)-1,2-dimethylhydrazinecarbothioamide | 147–152 | 0 |
| 75 | N—(2-Bromo-4-methylphenyl)-1,2-dimethylhydrazinecarbothioamide | 169–173 | 0 |
| 76 | N—(4-Bromo-2-methylphenyl)-1,2-dimethylhydrazinecarbothioamide | 149–152 | 0 |
| 77 | N—(4-Bromo-2,6-dimethylphenyl)-1,2-hydrazinecarbothioamide | 135–138 | 1.5 |
| 78 | 1,2-Dimethyl-N—(2-methylphenyl)hydrazinecarbothioamide | 122–126 | 2.5 |
| 79 | 1,2-Dimethyl-N—(4-methylphenyl)hydrazinecarbothioamide | 110–111 | 1 |
| 80 | 1,2-Dimethyl-N—(2,6-dimethylphenyl)hydrazinecarbothioamide | 157–161 | 1.25 |
| 81 | 1,2-Dimethyl-N—(3,4-dimethylphenyl)hydrazinecarbothioamide | 123–125 | 1 |
| 82 | 1,2-Dimethyl-N—(2,4,6-trimethylphenyl)hydrazinecarbothioamide | 127–133 | 0.9 |
| 83 | N—(4-Chlorophenyl)-1-methylhydrazinecarboxamide | 157–159 | 0 |
| 84 | N—(4-Chlorophenyl)-1,2-dimethylhydrazinecarboxamide | 92–94 | 2 |
| 85 | N—(4-Bromophenyl)-1-methylhydrazinecarboxamide | 147–149 | 0 |
| 86 | N—(4-Bromophenyl)-1,2-dimethylhydrazinecarboxamide | 105–106 | 0 |
| 87 | N—(2-Chlorophenyl)-1-methylhydrazinecarboxamide | 88–92 | 0.8 |
| 88 | N—(3-Chlorophenyl)-1-methylhydrazinecarboxamide | | 0.4 |
| 89 | N—(2,5 Dichlorophenyl)-1-methylhydrazinecarboxamide | 177–180 | 0.9 |
| 90 | N—(4-Methylphenyl)-1-methylhydrazinecarboxamide | 140–143 | 0.5 |
| 91 | N—(3,4-Dichlorophenyl)-1-methylhydrazinecarboxamide | 125–128 | 1 |
| 92 | N—(2-Chlorophenyl)-1,2-dimethylhydrazinecarboxamide | 79–81 | 0 |
| 93 | N—(3-Chlorophenyl)-1,2-dimethylhydrazinecarboxamide | 114–118 | 0 |
| 94 | N—(2,5-Dichlorophenyl)-1,2-dimethylhydrazinecarboxamide | 130–131 | 0 |
| 95 | N—(3,4-Dichlorophenyl)-1,2-dimethylhydrazinecarboxamide | 116–119 | 1 |
| 96 | N—(4-Methylphenyl)-1,2-dimethylhydrazinecarboxamide | 54–56 | 0 |
| 97 | N—(4-Bromo-2-methylphenyl)-1-(2-hydroxyethyl)hydrazinecarbothioamide | 89–95 | 0.8 |
| 98 | N—(2,4-Dichlorophenyl)-1-(2-hydroxyethyl)hydrazinecarbothioamide | 74–84 | 0.8 |
| 99 | N—(4-Chloro-2-methylphenyl)-1-(2-cyanoethyl)hydrazinecarbothioamide | 152–153 | 1 |
| 100 | N—(4-Bromo-2-methylphenyl)-1-(2-cyanoethyl)hydrazinecarbothioamide | 152–156 | 0.5 |
| 101 | 1,2-Dimethyl-N—(4-nitrophenyl)hydrazinecarbothioamide | 136–138 | 0 |

TABLE 2
Evaluation Against Stunt Nematode

| Compound Number | Rate of Application | Percent Control[a] |
|---|---|---|
| 1 | 20 ppm | 95.8 |
| 2 | 20 | 96.8 |
| 6 | 10 | 58.8 |
| 6 | 15 | 99.3 |
| 7 | 15 | 97.5 |
| 9 | 10 | 84.1 |
| 13 | 20 | 95.0 |
| 23 | 15 | 96.6 |
| 24 | 15 | 99.3 |
| 26 | 15 | 99.6 |
| 39 | 20 | 78.2 |
| 45 | 10 | 15.0 |
| 46 | 10 | 23.4 |
| 47 | 10 | 30.7 |
| 50 | 10 | 27.3 |
| | 10 | 72.6 |
| 51 | 10 | 40.2 |
| | 10 | 54.0 |
| 54 | 15 | 63.3 |
| 56 | 15 | 95.7 |
| 59 | 5 | 80.4 |
| 63 | 20 | 92.5 |
| 73 | 15 | 95.3 |
| 84 | 15 | 85.8 |
| 85 | 15 | 90.3 |
| 86 | 15 | 87.7 |
| 101 | 15 | 64.1 |

[a] Percent Control =

$$\left[\left(\frac{\text{Average Population Count in the Check}} - \frac{\text{Average Population Count in the Treatment}}\right) \bigg/ \frac{\text{Average Population Count in the Check}}\right] \times 100$$

TABLE 3
Evaluation Against Lesion Nematode

| Compound Number | Rate of Application | Percent Control[a] |
|---|---|---|
| 1 | 20 ppm | 85.1 |
| | 10 | 12.1 |
| 2 | 20 | 94.9 |
| | 10 | 56.6 |
| 6 | 15 | 72.4 |
| 7 | 15 | 64.8 |
| 9 | 10 | 0 |
| 13 | 20 | 35.8 |
| 23 | 15 | 73.8 |
| 24 | 15 | 76.4 |
| 26 | 15 | 71.7 |
| 39 | 20 | 64.0 |
| | 10 | 20.3 |
| 45 | 10 | 14.7 |
| 46 | 10 | 62.4 |
| 47 | 10 | 1.2 |
| 50 | 10 | 43.5 |
| | 10 | 65.1 |

TABLE 3-continued

Evaluation Against Lesion Nematode

| Compound Number | Rate of Application | Percent Control[a] |
|---|---|---|
| 51 | 10 | 63.6 |
|  | 10 | 84.8 |
| 54 | 15 | 53.5 |
| 56 | 15 | 78.2 |
| 59 | 5 | 26.3 |
| 63 | 20 | 43.7 |
| 73 | 15 | 59.0 |
| 84 | 15 | 73.8 |
| 85 | 15 | 0 |
| 86 | 15 | 64.7 |
| 101 | 15 | 49.7 |

[a]Percent Control =

$$\left[\frac{\frac{\text{Population count in check*}}{\text{Weight of roots in check plant}} - \frac{\text{Population count in treatment*}}{\text{Weight of roots in treated plants}}}{\frac{\text{Population Count in check}}{\text{Weight of Roots in Check Plant}}}\right] \times 100$$

*Average of 3–4 Replicates

What is claimed is:

1. A method of controlling nematodes which comprises applying to or incorporating into nematode-infested soil a nematicidally effective amount of a nematicidal composition including in admixture with an agriculturally acceptable carrier at least one nematicidal compound of the formula

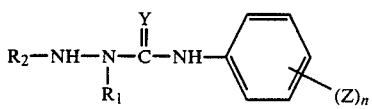

wherein
$R_2$ is H or $CH_3$,
Y is S or O,
n is 0–5,
Z is substituted for H and independently selected from F, Cl, Br, $CH_3$, $C_2H_5$ (when $R_2$ is H), $CF_3$, $NO_2$, and phenoxy,
and either
(1) $R_1$ is $CH_3$, with the provisos that when Y is S and n=1, Z is not 3-Cl if $R_2$ is $CH_3$; no more than one Z may be $C_2H_5$; when Y is O and n=2, Z is not 3-Cl and 5-Cl; and no more than one Z may be Br if $R_2$ is $CH_3$; or
(2) $R_1$ is $C_2H_4OH$ or $C_2H_4CN$, with the provisos that when Y=O and n=1, Z is not 4-Cl or 4-Br; and when n=2, Z is not 3-Cl and 4-Cl.

2. The method of claim 1 wherein Y is S.
3. The method of claim 1 wherein $R_1$ is $CH_3$.
4. The method of claim 1 wherein Z is selected from F, Cl, Br, and $CH_3$.
5. The method of claim 4 wherein n is 1 or 2.
6. The method of claim 1 wherein said composition comprises in admixture with an agriculturally acceptable carrier at least one nematicidal compound selected from N-(2,3-dichlorophenyl)-1-methylhydrazinecarbothioamide, N-(2,4-dichlorophenyl)-1-methylhydrazinecarbothioamide, N-(2,5-dichlorophenyl)-1-methylhydrazinecarbothioamide, N-(2,6-dichlorophenyl)-1-methylhydrazinecarbothioamide, N-(4-bromophenyl)-1-methylhydrazinecarbothioamide, N-(2,5-dibromophenyl)-1-methylhydrazinecarbothioamide, N-(2-chloro-6-methylphenyl)-1-methylhydrazinecarbothioamide, N-(3-chloro-2-methylphenyl)-1-methylhydrazinecarbothioamide, N-(4-chloro-2-methylphenyl)-1-methylhydrazinecarbothioamide, N-(5-chloro-2-methylphenyl)-1-methylhydrazinecarbothioamide, N-(4-bromo-2-methylphenyl)-1-methylhydrazinecarbothioamide, N-(4-chlorophenyl)-1,2-dimethylhydrazinecarbothioamide, N-(2,4-dichlorophenyl)-1,2-dimethylhydrazinecarbothioamide, N-2,5-dichlorophenyl)-1,2-dimethylhydrazinecarbothioamide, N-(3,4-dichlorophenyl)-1,2-dimethylhydrazinecarbothioamide, N-(4-bromophenyl)-1,2-dimethylhydrazinecarbothioamide, N-(2,6-difluorophenyl)-1,2-dimethylhydrazinecarbothioamide, N-(4-bromo-2-chlorophenyl)-1,2-dimethylhydrazinecarbothioamide, N-(3-chloro-2-methylphenyl)-1,2-dimethylhydrazinecarbothioamide, N-(4-chloro-2-methylphenyl)-1,2-dimethylhydrazinecarbothioamide, N-(5-chloro-2-methylphenyl)-1,2-dimethylhydrazinecarbothioamide, N-(4-bromo-2-methylphenyl)-1,2-dimethylhydrazinecarbothioamide, N-(3,4-dichlorophenyl)-1-methylhydrazinecarbothioamide, N-(4-chlorophenyl)-1-(2-hydroxyethyl)hydrazinecarbothioamide, N-(4-chlorphenyl)-1-(2-cyanoethyl)hydrazinecarbothioamide, N-(4-bromophenyl)-1-(2-cyanoethyl)hydrazinecarbothioamide, N-(2-chlorophenyl)-1,2-dimethylhydrazinecarbothioamide, N-(4-chlorophenyl)-1-methylhydrazinecarbothioamide, N-(4-chlorophenyl)-1,2-dimethylhydrazinecarboxamide, N-(4-bromophenyl)-1,2-dimethylhydrazinecarboxamide, N-(2-chlorophenyl)-1,2-dimethylhydrazinecarboxamide, N-(3-chlorophenyl)-1,2-dimethylhydrazinecarboxamide, N-(4-methylphenyl)-1,2-dimethylhydrazinecarboxamide, N-(4-bromo-2-methylphenyl)-1-(2-hydroxyethyl)hydrazinecarbothioamide, N-(2,4-dichlorphenyl)-1-(2-hydroxyethyl)hydrazinecarbothioamide, N-(4-chloro-2-methylphenyl)-1-(2-cyanoethyl)hydrazinecarbothioamide, N-(4-bromo-2-methylphenyl)-1-(2-cyanoethyl)hydrazinecarbothioamide, and 1,2-dimethyl-N-(4-nitrophenyl)hydrazinecarbothioamide.

7. The method of claim 1 wherein said composition comprises in admixture with an agriculturally acceptable carrier at least one nematicidal compound selected from N-(4-chlorophenyl)-1,2-dimethylhydrazinecarbothioamide, N-(4-chlorophenyl)-1-methylhydrazinecarbothioamide, N-(5-chloro-2-methylphenyl)-1-methylhydrazinecarbothioamide, N-(4-bromo-2-methylphenyl)-1-methylhydrazinecarbothioamide, N-(4-chlorophenyl)-1-(2-cyanoethyl)hydrazinecarbothioamide, N-(4-bromophenyl)-1-(2-cyanoethyl)hydrazinecarbothioamide, N-(4-chlorophenyl)-1,2-dimethylhydrazinecarboxamide, N-(4-bromophenyl)-1,2-dimethylhydrazinecarboxamide, N-(3-chlorophenyl)-1,2-dimethylhydrazinecarboxamide, N-(4-bromo-2-methylphenyl)-1-(2-hydroxyethyl)hydrazinecarbothioamide, and N-(2,4-dichlorophenyl)-1-(2-hydroxyethyl)hydrazinecarbothioamide.

8. The method of claim 1 wherein said composition comprises N-(4-chlorophenyl)-1,2-dimethylhydrazinecarbothioamide in admixture with an agriculturally acceptable carrier.

9. The method of claim 1 wherein said composition comprises N-(4-chlorophenyl)-1-methylhydrazinecarbothioamide in admixture with an agriculturally acceptable carrier.

10. The method of claim 1 wherein said composition comprises N-(5-chloro-2-methylphenyl)-1-methylhydrazinecarbothioamide in admixture with an agriculturally acceptable carrier.

11. The method of claim 1 wherein said composition comprises N-(4-bromo-2-methylphenyl)-1-methylhydrazinecarbothioamide in admixture with an agriculturally acceptable carrier.

12. The method of claim 1 wherein said composition comprises N-(4-chlorophenyl)-1-(2-cyanoethyl)hydrazinecarbothioamide in admixture with an agriculturally acceptable carrier.

13. The method of claim 1 wherein said composition comprises N-(4-bromophenyl)-1-(2-cyanoethyl)hydrazinecarbothioamide in admixture with an agriculturally acceptable carrier.

14. The method of claim 1 wherein said composition comprises N-(4-chlorophenyl)-1,2-dimethylhydrazinecarboxamide in admixture with an agriculturally acceptable carrier.

15. The method of claim 1 wherein said composition comprises N-(4-bromophenyl)-1,2-dimethylhydrazinecarboxamide in admixture with an agriculturally acceptable carrier.

16. The method of claim 1 wherein said composition comprises N-(3-chlorophenyl)-1,2-dimethylhydrazinecarboxamide in admixture with an agriculturally acceptable carrier.

17. The method of claim 1 wherein said composition comprises N-(4-bromo-2-methylphenyl)-1-(2-hydroxyethyl)hydrazinecarbothioamide in admixture with an agriculturally acceptable carrier.

18. The method of claim 1 wherein said composition comprises N-(2,4-dichlorophenyl)-1-(2-hydroxyethyl)-hydrazinecarbothioamide in admixture with an agriculturally acceptable carrier.

* * * * *